United States Patent
De Graaff et al.

(10) Patent No.: US 9,198,857 B2
(45) Date of Patent: Dec. 1, 2015

(54) GROWTH PROMOTION OF ANIMALS BY SIMULTANEOUS RELEASE OF STEROID COMPOUNDS FROM A DEVICE

(75) Inventors: Wouter De Graaff, Oss (FR); Marc-Antoine Driancourt, Beaucouze (NL); Raymond Zeeman, Oss (NL)

(73) Assignee: Intervet Inc., Madison, NJ (US)

( * ) Notice: Subject to any disclaimer, the term of this patent is extended or adjusted under 35 U.S.C. 154(b) by 525 days.

(21) Appl. No.: 13/256,286

(22) PCT Filed: Mar. 15, 2010

(86) PCT No.: PCT/EP2010/053240
§ 371 (c)(1),
(2), (4) Date: Nov. 22, 2011

(87) PCT Pub. No.: WO2010/105995
PCT Pub. Date: Sep. 23, 2010

(65) Prior Publication Data
US 2012/0058171 A1    Mar. 8, 2012

Related U.S. Application Data

(60) Provisional application No. 61/160,939, filed on Mar. 17, 2009.

(30) Foreign Application Priority Data

Mar. 17, 2009 (EP) ..................... 09155385

(51) Int. Cl.
| | |
|---|---|
| *A61K 45/06* | (2006.01) |
| *A61K 31/57* | (2006.01) |
| *A61K 9/00* | (2006.01) |
| *A61K 31/565* | (2006.01) |
| *A61K 31/567* | (2006.01) |
| *A61K 9/50* | (2006.01) |
| *A61K 47/32* | (2006.01) |

(52) U.S. Cl.
CPC ............. *A61K 9/0024* (2013.01); *A61K 9/0036* (2013.01); *A61K 9/5073* (2013.01); *A61K 31/565* (2013.01); *A61K 31/567* (2013.01); *A61K 45/06* (2013.01); *A61K 47/32* (2013.01)

(58) Field of Classification Search
None
See application file for complete search history.

(56) References Cited

U.S. PATENT DOCUMENTS

| 7,001,609 | B1 * | 2/2006 | Matson et al. ................ 424/434 |
| 2006/0280771 | A1 * | 12/2006 | Groenewegen et al. ...... 424/426 |

FOREIGN PATENT DOCUMENTS

| EP | 0 876 815 | 1/2002 |
| WO | WO 85/03440 | 8/1985 |
| WO | WO 2004/103336 | 12/2004 |
| WO | WO 2008/061963 | 5/2008 |
| WO | WO 2009/036999 | 3/2009 |

OTHER PUBLICATIONS

Van Laarhoven, J. et al. "In Vitro Release Properties of Etonogestrel and Ethinyl Estradiol from a Contraceptive Vaginal Ring", International Journal of Pharmaceutics, Elsevier B.V., NL, 232(1-2):163-173 (Jan. 31, 2002) XP002311934.
International Search Report corresponding to PCT/EP2010/053240, mailed Dec. 2, 2010.

* cited by examiner

*Primary Examiner* — Anna Pagonakis

(57) ABSTRACT

The present invention relates to a veterinary zoo-technical drug delivery system (device) for the simultaneous release of two or more active substances, which system releases the active substances in a substantially constant ratio over a prolonged period of time. The drug delivery system can be in different forms, such as e.g. an implant, or a intravaginal device such as a helical coil, a spring or a ring.

2 Claims, 3 Drawing Sheets

TBA in vitro release from a three-layered TBA-MGA containing controlled release device Figure 1: TBA in vitro release from a three-layered TBA-MGA containing controlled release device
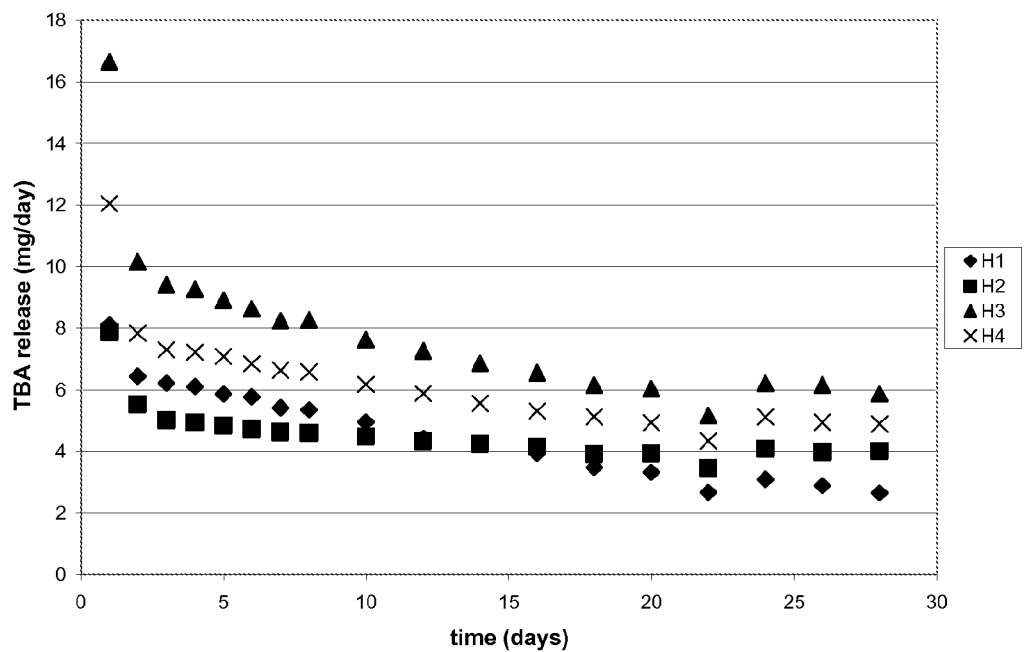
Figure 2: MGA in vitro release from a three-layered TBA-MGA containing controlled release device
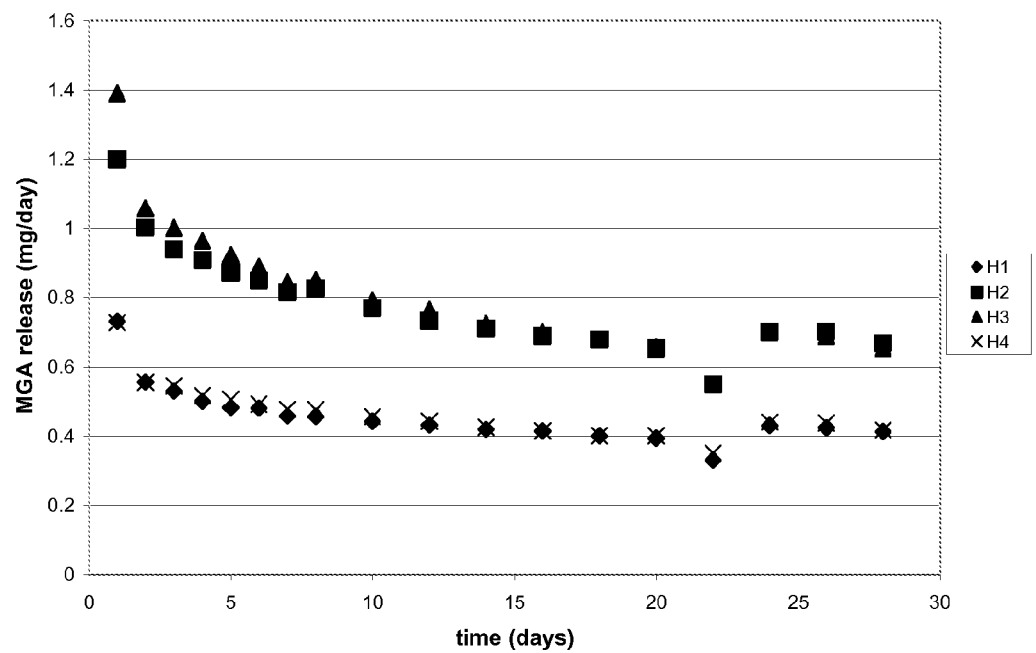

Figure 3: TBA in vitro release from a three-layered TBA-E2 containing controlled release device
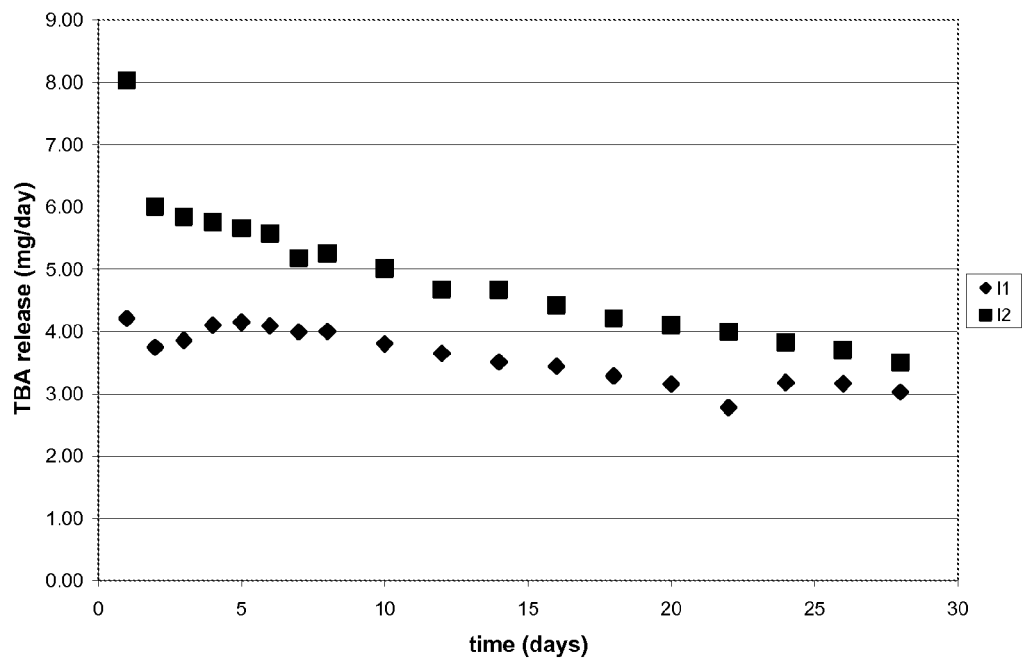
Figure 4: E2 in vitro release from a three-layered TBA-E2 containing controlled release device
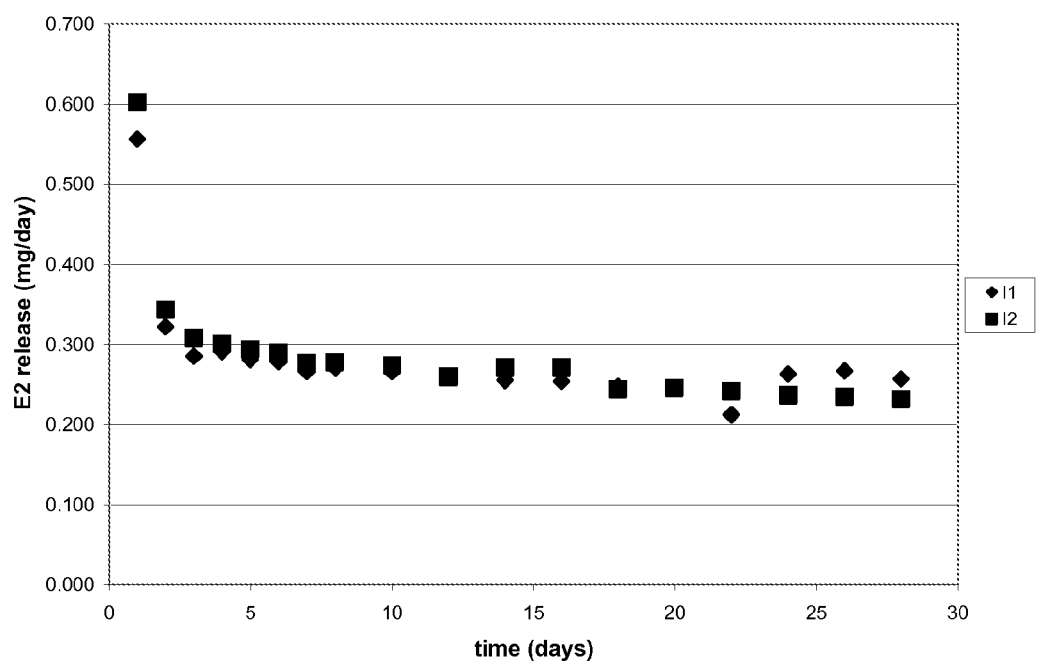

Figure 5: Fibre cross-section
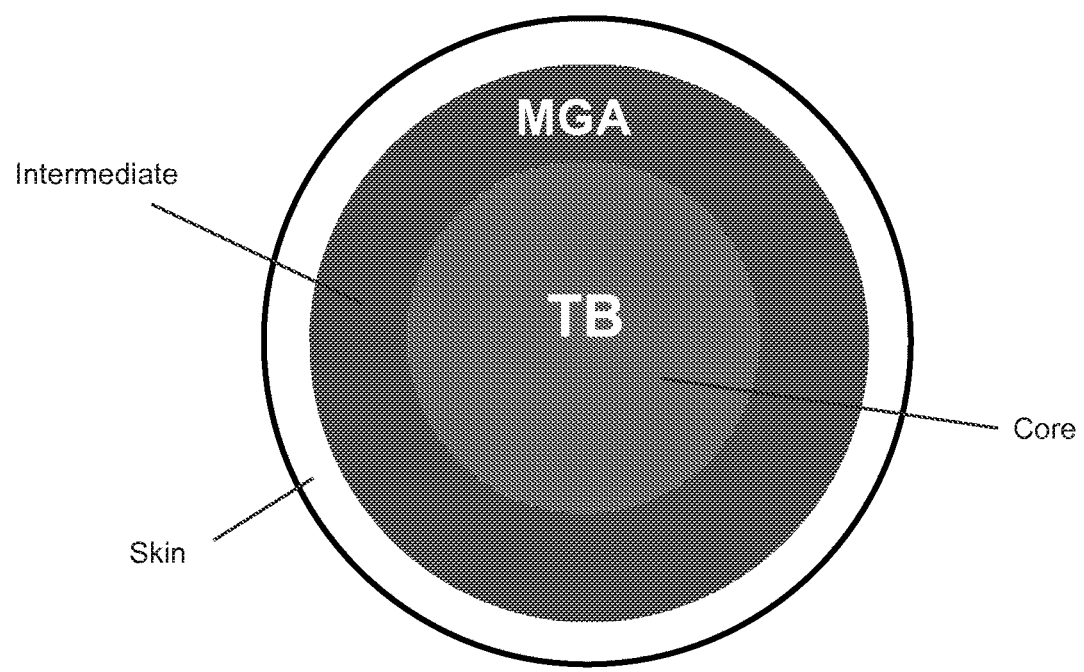

GROWTH PROMOTION OF ANIMALS BY SIMULTANEOUS RELEASE OF STEROID COMPOUNDS FROM A DEVICE

RELATED APPLICATIONS

This application is a national stage entry under 35 U.S.C. §371 of PCT/EP2010/053240 filed on Mar. 15, 2010, which claims priority to U.S. Provisional Application No. 61/160,939 filed on Mar. 17, 2009 (now expired) and to EP Application No. 09155385.9 filed on Mar. 17, 2009.

FIELD OF THE INVENTION

The present invention relates to a veterinary zoo-technical drug delivery system (device) for the simultaneous release of two or more active substances, which system releases the active substances in a substantially constant ratio over a prolonged period of time. The drug delivery system can be in different forms, such as e.g. an implant, or an intravaginal device such as a helical coil, a spring or a ring.

BACKGROUND OF THE INVENTION

Optimization of growth and food efficiency are of primary importance in livestock animals raised for meat.

Effective growth promoting zootechnical compositions are available, including the steroids estradiol and melengestrol acetate (MGA), trenbolone acetate (TBA), zeranol, and testosterone and other non-steroidal compounds e.g. zilpaterol, ractopamine, ionophore antibiotics, probiotics.

Similarly, estrus-related reduction of appetite in female livestock animals diminishes weight gain. U.S. Pat. No. 3,417,182 discloses the use of MGA for the control of estrous periods and the stimulation of growth for domestic birds and animals.

Some of these growth promoting zoo-technical compositions are administered via the feed to the livestock animals, e.g. zilpaterol hydrochloride and melengestrol acetate Some of these compositions are implantable in animals. Such implantable compositions are often administered as solid compressed pellets which are injected by an implanter equipped with a hypodermic needle. In livestock, implants are normally inserted in the ear or in other areas of the animal that are not for consumption and are discarded. The implanter needle is used to make a small self-sealing implant-receiving puncture beneath the skin at a suitable location on the body of the animal. Small pellets of a composition are forced through the needle and left under the skin as the needle is removed.

For example, TBA has been used in the form of an implantable composition with heifers, lambs, pigs, etc. to increase body weight gain in livestock as disclosed in U.S. Pat. No. 4,472,394. U.S. Pat. Nos. 4,900,735 and 5,147,869 disclose implantable compositions comprising TBA (TBA) and estradiol used to generate improved growth characteristics in feed lot cattle.

In the prior art it is stated that it would be desirable that one or more growth stimulating agents and one or more supplemental agents could be mixed together and incorporated in a single pellet for implantation; however, because each of the agents may be absorbed at different rates or require different carriers, normally there will be a different pellet, such as for each of the agents.

It would be desirable to identify a veterinary drug delivery system for release of two actives from the same compartment that allows for independent adjustment of this release from the device for compounds that are partly present in crystalline form.

Furthermore, there is a need for a system which releases both a growth stimulating dosage in combination with other compounds that improve the zoo-technical performance e.g. parasiticidal dosage, an antimicrobial dosage, an estrus suppressant dosage and/or other supplemental agents to provide control of parasites, microbial infection, estrus and maximize growth rate.

It is therefore the object of the present invention to provide a zootechnical drug delivery system in which the release rate of the two compounds that are partly present in the solid state and partly in the dissolved state can be regulated independently from one another from the same compartment.

SUMMARY OF THE INVENTION

This problem is solved by the invention, of a zoo-technical drug delivery system which comprises (i) a medicated thermoplastic polymer core layer, (ii) a medicated thermoplastic polymer intermediate layer and (iii) a non-medicated thermoplastic polymer skin covering the intermediate layer, wherein said core layer is loaded with crystals of a first zoo-technical active compound, and wherein said intermediate layer is loaded with crystals of a second zoo-technical active compound.

In a first embodiment of the invention the core layer forms the core of the drug delivery system. In an alternative embodiment, the drug delivery system comprises an additional non-medicated core that is covered by the core layer.

The drug delivery system according to the invention may also comprise more layers than the core, intermediate and skin layers mentioned above. The layers form a tri-or multi-axial fiber that is used for shaping a delivery system.

The drug delivery system of the invention is preferably a single compartment system, which means that the whole system consists of the same segment that is made of the same type of drug loaded reservoir e.g. a fiber. The fiber can consist of three, four or more layers, of which at least two layers are loaded with an active ingredient in crystalline form.

The subject invention thus provides a three-layer design drug delivery system from which two active compounds, in particular zoo-technically active compounds, can be released independently from one another.

The invention is particularly useful for simultaneous release of a zoo-technical active compound and another compound that have a relatively poor solubility in thermoplastic polymers (such as EVA polymers) and require a relatively high load in the polymeric matrix in order to obtain the desired release pattern, thus inevitably being present in their solid (crystalline) form in the polymer matrix.

Another object of the subject invention is to increase the efficiency of the drug substances employed in the drug delivery system and to minimize the remnant drug content in the used system.

It is an object of the present invention to provide a drug delivery system of which the release rate can be controlled to the requirements of a variety of non-human animals and various zoo-technical indications.

Furthermore, it is an object of the present invention to provide a veterinary system with a high ability to include a range of veterinary drugs and a high efficiency in delivering such drugs.

Even further, it is an objective of the present invention to provide a delivery system that can have high drug loading, and which can deliver the compounds at a controlled and useful rate over prolonged periods of time.

Another object of the subject invention is a method of improving the growth and weight gain in livestock animals by administering the zoo-technical drug delivery system according to the invention to an animal, especially a female cattle.

BRIEF DESCRIPTION OF THE DRAWINGS

FIG. 1 shows TBA in vitro release from a three-layered TBA-melengestrol acetate (MGA) containing controlled release device.

FIG. 2 shows MGA in vitro release from a three-layered TBA-melengestrol acetate (MGA) containing controlled release device.

FIG. 3 shows TBA in vitro release from a three-layered TBA-Estradiol (E2) containing controlled release device.

FIG. 4 shows E2 in vitro release from a three-layered TBA-Estradiol (E2) containing controlled release device.

FIG. 5 shows a fiber cross section comprising of a drug-loaded core layer (dark grey), a drug-loaded intermediate layer (light grey) and a non-medicated skin (white).

DETAILED DESCRIPTION OF THE INVENTION

The current invention provides a zoo-technical drug delivery system which comprises (i) a medicated thermoplastic polymer core layer, (ii) a medicated thermoplastic polymer intermediate layer and (iii) a non-medicated thermoplastic polymer skin covering the intermediate layer, wherein said core layer is loaded with crystals of a first zoo-technical active compound, and wherein said intermediate layer is loaded with crystals of a second zoo-technical active compound. In a first embodiment of the invention the core layer forms the core of the drug delivery system. In an alternative embodiment, the drug delivery system comprises an additional non-medicated core that is covered by the core layer.

Thus during manufacturing the drug crystals are not dispersed in a single layer, but crystals of the actives A and B are dispersed in two separated layers. A fraction of the actives A and B will dissolve in the polymer until the saturation concentration is reached and simultaneous internal diffusion will level out the internal concentration gradients. The crystals of the active compounds A and B are immobile and hence the crystals of the actives A and B stay spatially separated in the layers in which they were initially loaded.

The release kinetics of a drug delivery system intended for the simultaneous release of two active compounds is characterized by two essential attributes; the absolute rate in which the two compounds are released from the delivery system and the mutual ratio in which these compounds are released. The absolute release rate of the actives A and B from the delivery system can be tuned by adjusting the skin thickness. The ratio, in which these compounds are released, however, will remain essentially unaffected by skin thickness variations, because adjustment of the skin thickness affects the diffusion path of the compounds A and B equally.

Known solutions (EP 876 815, WO2005/089723 and WO2004/103336) for independent release tuning of two compounds from the same compartment are not suitable, since these solutions are based on the attribute that at least one compound is entirely dissolved in the delivery system. Obviously this is not the case for a system according to the object invention containing two actives both partly present in crystalline form. For this reason a new and alternative mechanism for adjusting the mutual release ratio had to be contemplated.

In the new concept independent adjustment of the release of two actives from the same compartment is achieved by the creation of a distinct diffusion path for the actives A and B. For this purpose A and B are loaded in the same compartment in two separate layers. In a delivery system with crystals of the active compounds A and B loaded in the core layer and intermediate layer respectively, compound A will develop a concentration gradient over both the intermediate layer and skin, while active B will develop a concentration gradient only over the skin. The different diffusion length of the compounds A and B provide a means to independently adjust the ratio in which these compounds are released from the system. The diffusion length of the compound loaded in the core layer can be adjusted by varying the thickness of the intermediate layer. Thus by varying the intermediate layer thickness the release rate of the compound loaded in the core layer can be tuned up or down, by decreasing or increasing intermediate layer thickness. The diffusion path of the compound loaded in the intermediate layer, however, remains essentially unchanged and hence the release rate also remains essentially unaffected. Thus, the release rate of the drug compound loaded in the core layer can be changed without affecting the release rate of the drug compound loaded in the intermediate layer and hence the release ratio can be adjusted towards the desired ratio. Once the desired release ratio is obtained, the absolute release rate can be adjusted by choosing the right skin thickness.

The subject drug delivery system thus solves the problem since it allows to adjust, independently from one another, the release rate of two active compounds, in particular zoo-technically active compounds, that are present in the crystalline state in the polymer, for example because they have a relatively poor solubility in EVA polymers and/or require a relatively high drug load in the polymeric matrix in order to obtain the desired release profile.

The zoo-technical active compound as used herein broadly includes one or more compounds that can be delivered in effective amounts to produce a zoo-technical, especially growth promoting effect. As used herein, the term zoo-technical active compound is intended to include such agents as noted above and other compositions that operably function under the present invention to promote physiological growth and which may be used internally in the particular species of animal to be treated by the invention.

In a preferred embodiment both zoo-technical active compounds are steroids. The steroids include e.g. progestogenic, androgenic and estrogenic substances. In a more preferred embodiment the drug is selected from the group consisting of progesterone, trenbolone acetate, zilpaterol hydrochloride, estradiol (E2), altrenogest, zeranol and melengestrol acetate (MGA).

In one embodiment the first zoo-technical active compound is trenbolone acetate and said second active compound is an estrogen, selected from the group consisting of estradiol, ethinyl estradiol, estriol, esters thereof.

In another embodiment the first zoo-technical active compound is trenbolone acetate (TBA) and said second zoo-technically active compound is a progestogen. In one embodiment the progestogen is nomegestrol acetate, altrenogest or melengestrol acetate.

Alternatively selective estrogen receptor modulators or selective androgen receptor modulators are involved.

It is noted that the amount of zoo-technical active compounds required to produce the desired treatment varies with respect to the species and size of the animal to be treated.

For example, in pasture cattle the zoo-technical active compound may be in a range from 5 to 50 milligrams per implant, preferably within the range of 10 to 30 milligrams and most preferred with a dosage of 20 milligrams. For pasture or feedlot heifers the zoo-technical active compound may be in a range of 20 to 400 milligrams per implant, preferably in a range of 40 to 100 milligrams for pasture heifers and 150 to 250 milligrams for feedlot heifers. For the cattle entering a feed yard the zoo-technical active compound may be in a range from 5 to 50 milligrams per implant, with a preferred range of 15 to 30 milligrams and a most preferred dosage of 25 milligrams.

In one embodiment TBA and MGA are comprised in the zoo-technical drug delivery device.

In the preferred embodiment, the composition is capable of providing sustained release properties so that the zoo-technical drug delivery device will yield desired results, more particularly growth promotion with estrus suppression and pregnancy inhibition in the animal for between about 60 to about 365 days with a more preferred range of from about 150 to about 200 days and a most preferred range of from about 180 to about 200 days.

The dosage of the MGA and TBA typically is the amount required to produce the desired effect. Because of the great fluctuation in weight from animal to animal, the amount given can vary widely. For most implants used in association with livestock, the amount of MGA in the implant is between about 5 and about 200 mg and the amount of TBA in the implant is between about 5 and about 200 mg. In embodiments where estradiol is also included, it is at an amount of about 5 and about 50 mg.

In another embodiment in addition to steroids, also non-steroidal compounds may be included in the drug delivery system of the invention, in particular for administering two or more active compounds in a particular ratio. Such compounds may be macrocyclic lactones such as ivermectin or moxidectin.

Such non-steroidal compounds can be other zootechnical compounds used for growth promotion such as zeranol, zilpaterol, especially zilpaterol hydrochloride, ractopamine, ionophore antibiotics, probiotics . . . . Zeranol is a non-steroidal estrogenic growth stimulant that is used in veterinary medicine In one embodiment the zootechnical drug delivery device is in the form of a subcutaneous implant. Such implants can be injected by an implanter equipped with a hypodermic needle. In livestock implants are normally made in the ear or in other areas of the animal that are not for consumption and are discarded. The implanter needle is used to make a small self-sealing implant-receiving puncture beneath the skin at a suitable location on the body of the animal. The implant of the current invention is forced through the needle and left under the skin as the needle is removed.

Optimization of growth patterns and of meat quality in female livestock animals may be alternatively obtained by using the vaginal route of delivery. In this case the intravaginal device can be in the form of a ring, a spring, a T-shaped device. A suitable helically shaped drug delivery system is described in WO 2008/061963, incorporated by reference herein.

In a first embodiment of the invention the core layer forms the core of the drug delivery system. In an alternative embodiment, the drug delivery system comprises an additional non-medicated core that is covered by the core layer.

In the new concept independent adjustment of the release of two actives from the same compartment is achieved by the creation of a distinct diffusion path for the actives A and B. For this purpose A and B are loaded in the same compartment in two separate layers. In a delivery system with crystals of the active compounds A and B loaded in the core layer and intermediate layer respectively, compound A will develop a concentration gradient over both the intermediate layer and skin, while active B will develop a concentration gradient only over the skin. The different diffusion length of the compounds A and B provide a means to independently adjust the ratio in which these compounds are released from the system.

The diffusion length of the compound loaded in the core layer can be adjusted by varying the thickness of the intermediate layer. Thus by varying the intermediate layer thickness the release rate of the compound loaded in the core layer can be tuned up or down, by decreasing or increasing intermediate layer thickness. The diffusion path of the compound loaded in the intermediate layer, however, remains essentially unchanged and hence the release rate also remains essentially unaffected. Thus, the release rate of the drug compound loaded in the core layer can be changed without affecting the release rate of the drug compound loaded in the intermediate layer and hence the release ratio can be adjusted towards the desired ratio. Once the desired release ratio is obtained, the absolute release rate can be adjusted by choosing the right skin thickness.

Another possibility to change the release ratio drastically is to reverse the drug load in the core layer and intermediate layer. Instead of loading active A in the core layer and B in the intermediate layer, B can be loaded in the core layer and A in the intermediate layer. A further means to tune the release ratio is to make use of different polymer grades used for the intermediate layer.

The diffusion path of the drug loaded in the core layer leads through the intermediate layer and skin. The composition of the intermediate layer, however, is not constant. During use or in-vitro release testing the size and concentration of solid particles loaded in the intermediate layer will gradually decrease to a fraction of the initial content and particle size. Surprisingly it was found that the release rate of the drug compound loaded in the core—which diffuses through a layer of variable composition—is not largely affected and remains essentially zero order.

Another object of invention is an increased efficiency of the drug delivery system, which means a lower residual drug content in the system after use.

Without being bound by theory the improved efficiency of the delivery system according to the object invention can be understood in terms of a stabilized concentration gradient in the delivery system. The new delivery system contains crystals of both compounds and hence a decrease of the dissolved concentration of both drugs due to diffusion out of the system will be counterbalanced by crystals going into dissolution. This means that the concentration gradient during (semi) steady state release remains essentially constant as long as the dissolution rate of the crystals is in conjunction with the drug transport out of the system.

The essence of this novel three-layered drug delivery system of the subject invention lies in the provision of the possibility to adjust the release rates of two zoo-technical active compounds independently from one another in spite of the fact that the compounds used in the subject invention are both present in their solid (crystalline) state in the polymer matrix because they have a relatively poor solubility in thermoplastic polymers and/or require a relatively high load in the polymeric matrix in order to obtain the desired release ratio and/or release rate, thus inevitably being present in the crystalline state.

The fibre can consist of three layers but may also comprise one or more additional layers. An example of an additional layer can be a non-medicated core that is covered by the medicated core layer. A non-medicated core can be advantageous for the efficiency of the drug delivery system. The core mainly acts to give the fibre its predetermined thickness, which means that the core comprises a large volume. A large core reservoir (in a three-layer design) should contain the drug substance in such a level that crystalline material is and remains present. This could mean that a large excess of drug substance is needed. In case an additional non-medicated core (fourth layer) is present, the inner medicated layer must contain the drug substance at a higher concentration, without affecting the release rates. Due to this higher concentration, the average diffusion path is shorter and the release rate might be even more constant. A higher drug substance efficiency can thus be achieved without influencing the release profiles significantly.

In another embodiment, additional layers may be comprised between the medicated layers. This can be used as a further means to differentiate the diffusion path for the compound loaded in core-layer and intermediate shell.

According to the invention, various other configurations are possible provided that at least two layers are medicated and that the active compounds in these layers are at least partially present in the solid state.

A drug delivery system of the subject invention can be used in any mammal, the intravaginal device in particular a female mammal. In a specific embodiment, the mammal is a cow, a heifer, a sow, a mare or a female goat or sheep.

The drug delivery system of the invention can be provided in various forms that are made from the multi- or three-layered fiber that comprises a medicated core layer, a medicated intermediate layer and a non-medicated skin. The core layer may be the core or may cover a non-medicated core. Suitable forms comprise substantially ring-shaped forms, rods, T-shapes etc.

Forms that are appropriate for vaginal administration, such as for example helically coiled spirals and ring devices having convoluted surface. Implants have usually a rod-shaped form.

The provision of a fiber as used in a drug delivery system of the subject invention is accomplished by (1) loading the core of the fiber with a first (zoo-technically) active compound in solid (crystalline) form and (2) loading the intermediate layer of the fiber with a second zoo-technically active compound in solid form, thereby providing a fiber wherein both compounds are physically separated and present in their solid form in two distinct layers, i.e. the core and the intermediate layer. The dissolved part of both zoo-technically active compounds is present all over the fiber in all layers once equilibrium is reached. The solid part of both drug substances remains separated.

In a specific embodiment of the subject invention, the (zoo-technically) active compounds have a relatively poor solubility in thermoplastic polymers such as EVA polymers and require a relatively high load in the polymeric matrix in order to obtain the desired release ratio. In a more specific embodiment of the invention, both zoo-technically active compounds are steroids.

However, the invention can as be used to release other active compounds that need to be administered concomitantly and in a particular ratio The desired release ratio depends on the indication sought to be used with the drug delivery device of the subject invention, such as growth promotion.

The release of steroids from the ring is influenced by the solubility and diffusion coefficient of the steroid in the polymer. In a specific case of steroids that have a relatively poor solubility in the polymer matrix and which require a relatively high load in the polymeric matrix in order to obtain the desired release pattern, the steroids will be incorporated into the matrix in their solid form and will be dissolved in the polymeric matrix until saturation is reached. In such a system the dissolved concentration cannot be chosen freely, but is equal to the saturation concentration.

Consequently, the steroid load cannot be used to tune the release to the desired rate, because varying the steroid load will not result in a higher or lower dissolved steroid concentration, as the steroid concentration will remain equal to the saturation concentration. Variation of the skin thickness will have a limited contribution to the adjustment of the release rate of more than one of such zoo-technically active compound independently from one another because an increase or a decrease of the skin thickness will in general influence the release of both compounds in the same direction.

After the ring has been put in a sink, steroid will start to diffuse out of the ring and the concentration of the steroid dissolved in the polymeric matrix will drop slightly. As a consequence thereof, the solid steroid will start to dissolve. Thus, the decrease of the concentration gradient due to diffusive transport out of the ring is counterbalanced by the dissolution of the steroid present in a solid form Hence, the concept of the three-layer vaginal ring of the invention is to load: (1) the core with a first steroid (A) that has a relatively poor solubility in EVA polymers and requires a relatively high load in the polymeric matrix in order to achieve the desired release profile; and to load (2) the intermediate layer with a second steroid (B) that has a relatively poor solubility in EVA polymers and requires a relatively high load in the polymeric matrix in order to achieve the desired release profile. Thus, both compound A and compound B are present in the polymer matrix in a solid state.

As will be appreciated, the desired release rates of steroid A and steroid B are obtained by separately placing the compounds in two distinct layers. The release rates may further be adjusted by varying the thickness and/or by varying the grade of the EVA polymer intermediate layer.

The three-layer vaginal ring of the invention can be designed to afford different ratios between the average release rates of compound A and compound B. The ratio between the average release rates of the steroidal compounds may be influenced by varying the location of the compounds, i.e. by loading compound A in the core and compound B in the intermediate layer or vice versa. The release ratio can be further adjusted by varying the intermediate layer thickness and/or by varying the intermediate layer polymer grade.

Further, the optimization of a ring intended for the simultaneous release of two compounds towards certain pre-set release specifications, requires the possibility to adjust both the relative ratio in which two drug compounds (A and B) are released as well as the possibility to tune the absolute rate in which the compounds are released daily.

If on the other hand, both steroids with relatively low solubility in the polymer matrix were loaded relatively high, together, in one single layer (i.e. in the intermediate layer or in the core), consequently both being present in their solid (crystalline) state, the release rate would be mainly governed by the solubility and diffusivity of the steroids in the polymer matrix. In such a case, only by shear coincidence would the desired release ratio be obtained and it would not result in the desired release rate for both compounds.

The drug delivery device of the subject invention can be manufactured by the known process of extrusion, such as co-extrusion and/or blend-extrusion. The drug-loaded core, the drug-loaded intermediate layer and the non-medicated outer layer are all co-extruded. The fibers thus obtained are cut into pieces of the required length and each piece is assembled to a ring-shaped device in any suitable manner. The rings are then packed for example in a suitable sachet, optionally after being sterilized or disinfected.

Drug delivery device ring of the subject invention can also be manufactured by using multi stage injection molding (Woolfson et al. (1999), J of Contr. Release 61: 319-328; Malcolm et al. (2003), J. Contr. Release 91: 355-364; Woolfson et al. (2003), J. Contr. Release 91: 465-476).

The thermoplastic polymer that can be used in practicing the invention may in principle be any thermoplastic polymer or elastomer material suitable for pharmaceutical use, such as low density polyethylene, ethylene-vinyl acetate copolymers, poly(ether urethane), styrene-butadiene-styrene copolymers and polysiloxanes. In a specific embodiment, ethylene-vinyl acetate copolymer (poly-EVA) is used due to its excellent mechanical and physical properties. The poly-EVA material may be used for the core, the intermediate layer as well as the skin and can be any commercially available ethylene-vinyl acetate copolymer, such as the products available under the trade names: Elvax, Evatane, Lupolen, Movriton, Ultrathene, Ateva and Vestypar.

In one embodiment both core and intermediate layer are made out of the same polymer grade. In another embodiment, the core and the intermediate layer are not made out of the same polymer grade. Electing different polymer grades for core and intermediate layer, provides a means to adjust the release rates of drug compounds from the drug delivery system and allows fine-tuning of the flexibility of the system of the invention.

The drug delivery system according to the invention can be manufactured in any size as required. The same applies to the other shapes.

An implant suitably has a length of 1 to 10 cm and a diameter of 1-4 mm, preferably a length of 1-8 cm and a diameter of 1-5 mm, Another object of the present invention is to increase the efficiency of the drug substances employed in the drug delivery system, and to minimize the remnant drug content in the used system. The remnant content of both drug A and drug B in a drug delivery system of the invention after use can be minimized to about 35 wt % or less of the amount loaded. Specifically, it can be reduced to about 10-30% by weight.

The drug delivery systems according to the invention are physically stable. As used herein, a physically stable drug delivery system is a system, which can be stored at about 18° C.-40° C. for at least about half a year to one year without steroid crystal formation on the surface of the skin of the delivery device.

The subject invention also provides a method of manufacturing the three-layered fiber that is used to make the drug delivery system of the subject invention by:
(i) producing a loaded (medicated) homogenous polymer core granulate
(ii) producing a loaded (medicated) homogenous polymer intermediate layer granulate; and
(iii) co-extruding the core granulate and the intermediate layer granulate with a polymer skin granulate to form the three-layered fiber.

The production of the loaded (medicated) homogenous polymer core granulate comprises:
a) grounding the core polymer;
b) dry powder mixing the grounded polymer with the active compounds to be loaded in the core;
c) blend extruding the resulting powder mixture of step (b);
d) cutting the resulting loaded polymer strands into granules, thereby obtaining a core granulate;
e) lubricating the core granulate with a lubricant.

The production of the loaded (medicated) homogenous polymer intermediate layer granulate comprises:
a) grounding the intermediate layer polymer;
b) dry powder mixing the grounded polymer with the active compounds to be loaded in the intermediate layer;
c) blend extruding the resulting powder mixture of step (b);
d) cutting the resulting loaded polymer strands into granules, thereby obtaining a intermediate layer granulate;
e) lubricating the intermediate layer granulate with a lubricant.

The present invention is further described in the following examples, which are not in any way intended to limit the scope of the invention as claimed.

EXAMPLES

Example 1

Preparation of the Three-Layered Device

A variety of three-layered fibers were prepared (H1-H4, I1-I2). The fibers were stretched to 4.0 mm from a single 3.6 mm capillary.

In order to mix the active ingredients homogeneously through the polymer, two subsequent mixing steps were performed. In the first step, dry powder mixing was performed with the active compounds and polymer (EVA 28 or 33) powder. The active compounds were mixed with polymer powder in a stainless steel drum using a Rhonrad (Barrel-hoop principle) with a fixed rotation speed of approximately 47 rpm for 60 minutes. The first powder mixing step was performed by mixing the polymer and the active compound for the different active layers. Subsequently the homogenized powder mixtures were blend extruded using a 25 mm co-rotating double screw blend extruder (Berstorff ZE25) and the resulting medicated polymer strands were cut into granules using an IPS granulator. According to this process three active granulate batches were manufactured.

After granulation, all batches were lubricated with 0.1 wt % magnesium stearate in order to facilitate trico-extrusion. The compositions of the granulate batches that were used to manufacture the tri-layer fiber, using a co-extrusion process, are described in Table 1.

TABLE 1

Composition of active granulate batches

| Material | Active | Active content | EVA grade |
|---|---|---|---|
| Active granulate M | Estradiol (E2) | 10 wt % | EVA 28 |
| Active granulate O | Trenbelone acetate (TBA) | 35 wt % | EVA 33 |
| Active granulate P | Melengestrol acetate (MGA) | 25 wt % | EVA 28 |

Tri-Layer Co-Extrusion

A Fourne Trico extruder (18/18/15 mm screws) was used for co-extrusion of the three-layered fiber. The two 18 mm extruders processed the core and intermediate material, while the 15 mm extruder was used to process the skin layer. The three extruders were connected with a 3-compartment spinning block with 3 separate spinning pumps. These pumps were used to control the volume flow rate of the three polymer melts. By controlling volume flow rate the layer thickness of all three layers was adjusted. The three polymer melt flows were combined in the spinneret to form a 3-layered fiber. A capillary of 3.6 mm was used. The target fiber diameter was 4.0 mm and all fibers were extruded at a speed of 1-2 m/min.

Fiber dimensions (outer diameter, intermediate thickness and skin thickness) were measured on 6 fiber pieces. The outer diameter was determined by means of laser thickness equipment. The layer thicknesses were determined using a microscope (Jena).

The following fiber batches were manufactured:

TABLE 2

Composition of fiber batches produced by co-extrusion

| Variant | Skin thickness [μm] | Skin material (placebo) | Intermediate layer thickness [μm] | Intermediate material | Core material |
|---|---|---|---|---|---|
| H1 | 300 | EVA 28 | 550 | P | O |
| H2 | 150 | EVA 28 | 550 | P | O |
| H3 | 150 | EVA 28 | 275 | P | O |
| H4 | 300 | EVA 28 | 275 | P | O |
| I1 | 350 | EVA 28 | 600 | M | O |
| I2 | 350 | EVA 28 | 400 | M | O |

Cutting and Assembly

The three-layered fiber batches were cut into pieces of 157 mm after which they were welded with flash free welding machines at a welding temperature of approximately 125° C.

Example 2

In-Vitro Release Rates

The in vitro release rates from the obtained devices was determined in water containing 0.45% SLS.

In tables 3-6 the average in vitro release of the batches H and I is listed.

The device designs of Batch H represent formulations wherein MGA and TBA crystals are physically/spatially separated and are present in two distinct layers. The in vitro release results of H1 and H4 show that the TBA release can be increased while the MGA release remains largely unaffected as is shown in Table 3. The in vitro results of H2 and H3 show the same behavior. This shows that by physical separation of the two active compounds the release rate of the compounds can be adjusted independently.

TABLE 3

Average in vitro release rates from a three-layered ring containing MGA and TBA

| | Melengestrol acetate release [mg/day] | | | Trenbelone acetate release [mg/day] | | |
|---|---|---|---|---|---|---|
| Batch: | Day 1 | Average day (2-28) | Day 28 | Day 1 | Average day (2-28) | Day 28 |
| H1 | 0.730 | 0.431 | 0.412 | 8.10 | 4.16 | 2.65 |
| H2 | 1.20 | 0.738 | 0.668 | 7.87 | 4.28 | 4.01 |
| H3 | 1.39 | 0.753 | 0.653 | 16.65 | 7.06 | 5.87 |
| H4 | 0.727 | 0.441 | 0.417 | 12.03 | 5.70 | 4.88 |

TABLE 4

Average in vitro release rates from a three-layered ring containing MGA and TBA

| | Estradiol release [mg/day] | | | Trenbelone acetate release [mg/day] | | |
|---|---|---|---|---|---|---|
| Batch: | Day 1 | Average day (2-28) | Day 28 | Day 1 | Average day (2-28) | Day 28 |
| I1 | 0.556 | 0.261 | 0.257 | 4.21 | 3.48 | 3.03 |
| I2 | 0.603 | 0.263 | 0.232 | 8.04 | 4.58 | 3.51 |

The device designs of Batch I represent formulations wherein E2 and TBA crystals are physically/spatially separated and are present in two distinct layers. The in vitro release results of I1 and I2 show that the TBA release can be increased while the E2 release remains largely unaffected as is shown in Table 4.

Release Ratio

Table 5 and 6 show the ratio of the in vitro release of the two active substances present in the same device.

TABLE 5

Ratio of the in vitro release rate of TBA and MGA

| Batch | Average MGA day 2-28 release [mg/day] | Average TBA day 2-28 release [mg/day] | Ratio of TBA and MGA (day 2-28 release) |
|---|---|---|---|
| H1 | 0.431 | 4.16 | 9.65 |
| H2 | 0.738 | 4.28 | 5.80 |
| H3 | 0.753 | 7.06 | 9.38 |
| H4 | 0.441 | 5.70 | 12.93 |

TABLE 6

Ratio of the in vitro release rate of TBA and E2

| Batch | Average E2 day 2-28 release [mg/day] | Average TBA day 2-28 release [mg/day] | Ratio of TBA and E2 (day 2-28 release) |
|---|---|---|---|
| I1 | 0.261 | 3.48 | 13.33 |
| I2 | 0.263 | 4.58 | 17.41 |

The invention claimed is:

1. A method of improving the growth and weight gain in livestock animals by administering to an animal, a zoo-technical drug delivery system in the form of a subcutaneous implant which comprises
   (i) a medicated thermoplastic polymer core layer,
   (ii) a medicated thermoplastic polymer intermediate layer; and
   (iii) a non-medicated thermoplastic polymer skin covering the intermediate layer, wherein said core layer is loaded with crystals of a first zoo-technical active compound, wherein said intermediate layer is loaded with crystals of a second active compound, wherein the first zoo-technical active compound is trenbolone acetate and the second zoo-technical active compound is altrenogest, wherein the medicated thermoplastic polymer core layer and intermediate layer each comprise ethylene-vinyl acetate copolymer; and wherein the implant is administered subcutaneously to the animal.

2. The method according to claim 1 characterized in that the animal is a female cattle.

* * * * *